United States Patent [19]
Levy

[11] Patent Number: 6,001,233
[45] Date of Patent: Dec. 14, 1999

[54] GEL ELECTROPHORESIS APPARATUS HAVING CAM-ACTIVATED CLAMP AND METHODS OF USE

[75] Inventor: Douglas R. Levy, Oceanside, Calif.

[73] Assignee: Novex, San Diego, Calif.

[21] Appl. No.: 09/059,604

[22] Filed: Apr. 13, 1998

[51] Int. Cl.[6] .............................. G01N 27/00; B25B 1/08
[52] U.S. Cl. ......................... 204/618; 74/107; 269/236
[58] Field of Search ................................ 204/618, 606, 204/616, 615, 456, 466, 467; 74/107, 567; 254/104; 248/222.11, 222.13; 269/236, 235

[56] References Cited

U.S. PATENT DOCUMENTS

| | | | |
|---|---|---|---|
| D. 261,609 | 11/1981 | Roux ........................................ | 269/236 |
| 344,713 | 6/1886 | Blythe ..................................... | 269/236 |
| 4,399,989 | 8/1983 | Baillie ..................................... | 269/236 |
| 4,772,373 | 9/1988 | Ebata et al. ............................. | 204/618 |
| 4,872,358 | 10/1989 | Buis ........................................ | 74/107 |
| 4,884,792 | 12/1989 | Rendahl et al. ......................... | 269/236 |
| 5,112,470 | 5/1992 | Sylvester ................................ | 204/618 |
| 5,632,877 | 5/1997 | Van Atta ................................. | 204/618 |
| 5,792,332 | 8/1998 | Montecino et al. .................... | 204/618 |
| 5,888,369 | 3/1999 | Tippins et al. .......................... | 204/606 |

FOREIGN PATENT DOCUMENTS 6-024768 6/1994 Japan .
293210 12/1953 Switzerland ........................... 269/236

OTHER PUBLICATIONS

"Biodirectory," Pharmacia Biotech Catalog, pp. 497–499 (1995).
"Ready Gel Cell Instruction Manual," Bio–Rad Laboratories (1996).
"Mini–Protean II Electrophoresis Cell Instruction Manual," Bio–Rad laboratories (1997).
"NOVEX Electrophoresis: The Right System, The Right Price," NOVEX Brochure (1997).

Primary Examiner—Terrence R. Till
Assistant Examiner—Andrew Aldag
Attorney, Agent, or Firm—Fish & Neave; James Trosino

[57] ABSTRACT

An apparatus for clamping electrophoresis gel cassettes to a buffer core body is provided that does not require separate clamping subassemblies. The apparatus comprises a cam pivotally coupled to a mounting block. The apparatus is inserted into an electrophoresis container and is positioned adjacent a buffer core assembly that includes gel cassettes disposed on opposite sides of a buffer core body. The cam is disposed to engage a back wall of the container to cause the mounting block to apply uniform pressure to secure the gel cassettes to the buffer core body. A method for securing an electrophoresis gel cassette to a buffer core body in an electrophoresis container is also disclosed.

20 Claims, 4 Drawing Sheets

GEL ELECTROPHORESIS APPARATUS HAVING CAM-ACTIVATED CLAMP AND METHODS OF USE

This invention relates to apparatus for performing electrophoresis. More particularly, this invention relates to a novel cam device for clamping gel cassettes in a gel electrophoresis system.

BACKGROUND OF THE INVENTION

Gel electrophoresis is commonly used to separate by molecular size biological molecules, such as deoxyribonucleic acid ("DNA"), ribonucleic acid ("RNA") and proteins. To perform gel electrophoresis, a polymeric gel, such as polyacrylamide, is formed in a glass tube, or between spaced glass or plastic plates. The tube or plates are then placed in a container along with anode and cathode elements at the top and bottom of the gel. Sample wells formed in the top of the gel are first filled with buffer solutions. Molecule samples prepared in a sample buffer that may contain a tracking dye are then placed in the wells. Electrophoretic buffer solutions containing conductive ions are added to the container to make electrical contact between the gel, the samples in the wells and the anode and cathode elements. A voltage is then applied across the gel, which causes the sample molecules and any tracking dye to migrate toward the bottom of the gel, and separate into bands whose migration distance depends on molecular size.

Previously known commercial gel electrophoresis systems, such as the XCell II Mini-Cell™ manufactured by Novel Experimental Technology, Incorporated, San Diego, Calif. ("NOVEX"), include a container for receiving a first buffer solution and a buffer core assembly that comprises a pair of gel cassettes affixed to front and back sides of a U-shaped buffer core. The space defined by the upraised side members of the buffer core and the end faces of the gel cassettes forms an upper buffer chamber. The buffer core assembly is immersed in the first buffer solution in the container, and a second buffer solution is added to the upper buffer chamber.

For accurate electrophoretic separation, the first and second buffer solutions must be isolated from one another. To provide isolation, prior art electrophoresis systems use various methods to hold the gel cassettes in contact with the buffer core and secure the buffer core assembly in the container. Previously known electrophoresis systems commonly use a buffer core subassembly containing clamps or latches that secure the gel cassettes to the buffer core. Once the cassettes are secured, the buffer core subassembly must then be loaded in the container prior to electrophoretic separation.

For example, the SE 200 Series Mini-Gel System manufactured by Hoefer Pharmacia, San Francisco, Calif., includes a buffer core subassembly that uses four spring clamps to secure a pair of gel cassettes to a buffer core. Similarly, the Mini-PROTEAN II Electrophoresis Cell manufactured by Bio-Rad, Hercules, Calif. ("Bio-Rad"), includes a buffer core subassembly that uses latches to secure gel cassettes to a buffer core. Alternatively, the Ready-Gel Cell manufactured by Bio-Rad, includes a buffer core subassembly having a pair of cams that secure gel cassettes to a buffer core. In each of these prior art systems, the user must first construct a clamping subassembly that is then loaded into the container prior to performing electrophoresis. It would be desirable to provide a clamping device that is easier to use and does not require separate clamping subassemblies.

Other prior art electrophoresis systems avoid the need for separate clamping subassemblies by using the electrophoresis container as part of the clamping mechanism. For example, the XCELL II Mini-Cell™ uses two wedge blocks inserted in the electrophoresis container to secure the gel cassettes against the buffer core. The wedge blocks, however, must be carefully inserted to obtain proper clamping action. For example, if the wedge blocks are not properly inserted, they may slip relative to one another, and may release pressure on the gel cassettes and degrade isolation between the first and second buffer solutions. Further, the wedge blocks provide a clamping force that varies depending on the amount of force used to insert the wedge blocks into the container. If too much force is applied, the components of the electrophoresis system may become overstressed and may eventually fracture. If too little force is applied, the gel cassettes may not be securely held in contact against the buffer core.

An improvement on the foregoing wedge block design is described in Japanese Patent Publication 62-201055 (Application No. 61-088779), in which two fastening screws adjust the pressure applied by the upper wedge block and ensure that the wedge blocks maintain continuous pressure on the gel cassettes and buffer core. Although a stop screw is provided in that device to provide reproducible pressure to the wedge blocks, the stop screw may inadvertently loosen or tighten with repeated use, thus varying the applied force from a predetermined value. Accordingly, if too much force is applied, the components of the electrophoresis system may become over-stressed and fracture. Conversely, if too little force is applied, the gel cassettes may not be securely held in contact against the buffer core.

In view of the problems associated with prior art clamping methods and apparatus, it is desirable to provide for gel electrophoresis systems a single cam-activated clamp that requires no clamping subassembly to reliably secure electrophoresis gel cassettes to a buffer core.

It is further desirable to provide for gel electrophoresis systems a single cam-activated clamp that provides a consistent and reproducible clamping force each time the apparatus is used.

It is also desirable to provide for gel electrophoresis systems a single cam-activated clamp that provides a positive stop to prevent overstressing the electrophoresis system components.

SUMMARY OF THE INVENTION

In view of the foregoing, it is an object of the present invention to provide for gel electrophoresis systems a single cam-activated clamp that requires no clamping subassembly to reliably clamp electrophoresis gel cassettes to a buffer core.

It is further an object of the present invention to provide for gel electrophoresis systems a single cam-activated clamp that provides a consistent and reproducible clamping force each time the apparatus is used.

It is also an object of the present invention to provide for gel electrophoresis systems a single cam-activated clamp that provides a positive stop to prevent overstressing the electrophoresis system components.

These and other objectives of the invention are accomplished by providing a cam-activated device that includes a cam arm assembly having a pair of spaced-apart cam arms pivotally coupled to a mounting block. The cam device is adapted for insertion into an electrophoresis container and is positioned adjacent a buffer core assembly that includes first and second gel cassettes disposed on opposite sides of a buffer core body. A cam is attached to the cam arms and has a curved end that slidingly engages the back wall of the electrophoresis container as the cam arm assembly is pivoted forward toward the front wall of the container. As the curved end engages the back wall of the container, the mounting block applies uniform pressure to the first gel cassette and the buffer core body. Simultaneously, the second gel cassette abuts fixed vertical ridges formed in the side walls of the container, thereby securing the mounting block against the buffer core assembly and clamping the gel cassettes to the buffer core body. Flat surfaces provided on forward-facing edges of the cam arms contact a back surface of the mounting block, thereby providing a positive stop.

These and other aspects and advantages of the invention will become apparent from the following detailed description, and the accompanying drawings, which illustrate by way of example the features of the invention.

DETAILED DESCRIPTION OF A PREFERRED EMBODIMENT

Figure 1:
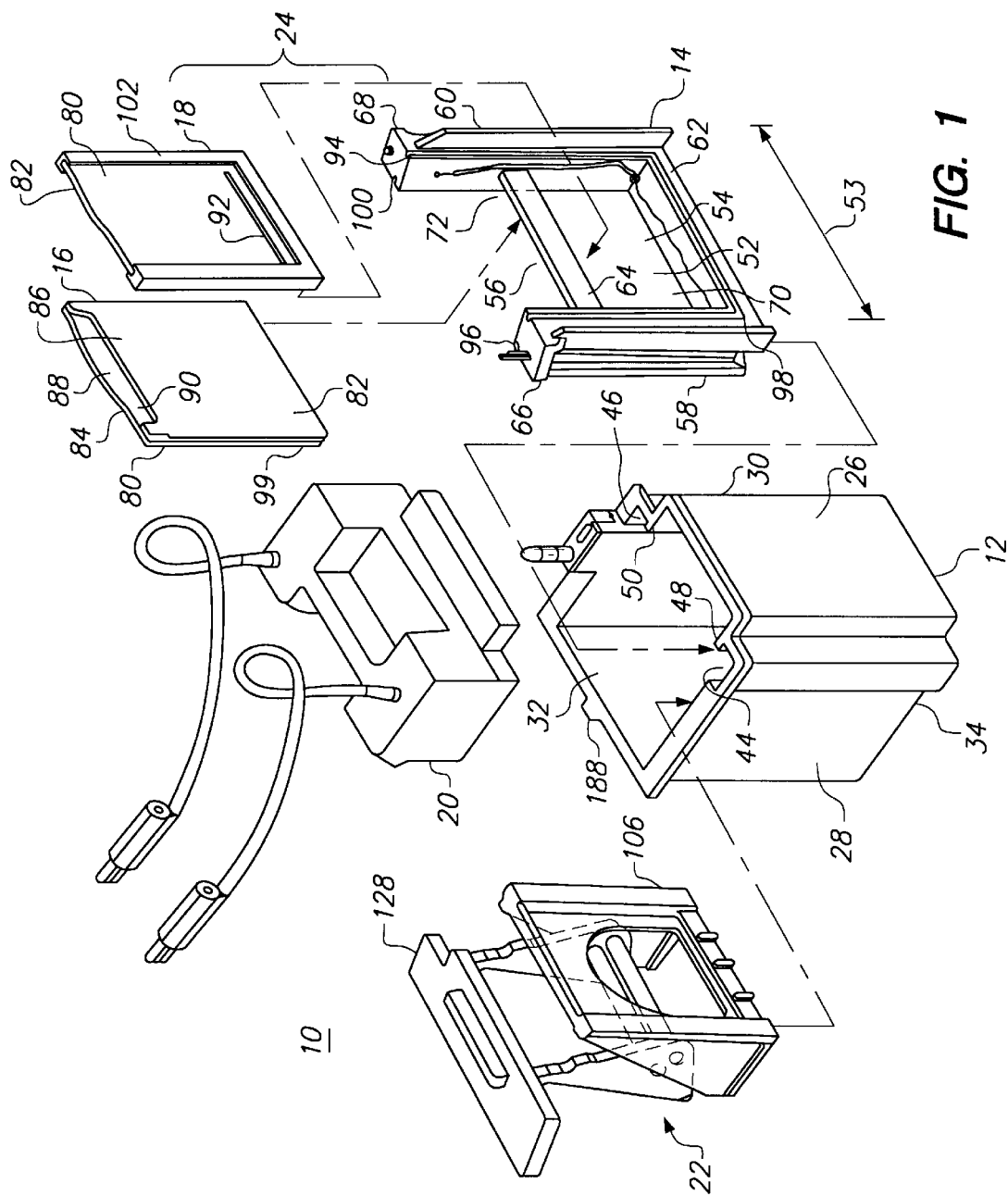
FIG. 1 is an exploded perspective view of an electrophoresis cell assembly that includes an exemplary embodiment of the cam device of this invention.

An electrophoresis system including an exemplary embodiment of the present invention is shown in FIG. 1. The system 10 comprises container 12, buffer core body 14, gel cassettes 16 and 18, lid 20, and cam device 22, constructed in accordance with the principles of the present invention. Buffer core body 14 and gel cassettes 16 and 18 collectively form buffer core assembly 24.

Container 12 includes front wall 26, side walls 28 and 30, back wall 32 and closed bottom 34. Container 12 is open at the top for receiving a first electrophoresis buffer solution (not shown). Located on opposite inner surfaces of side walls 28 and 30 and spaced away from the front wall 26 of container 12 are wall recesses 44 and 46. Wall recesses 44 and 46 are aligned with each other to receive buffer core assembly 24 and are integrally formed with side walls 28 and 30, respectively. Each of the wall recesses has a cross-section of an irregular C-channel when viewed from the top of container 12.

Wall recesses 44 and 46 are sized to accommodate the lateral width 53 of buffer core assembly 24 without significant lateral movement. The width of wall recesses 44 and 46 is slightly greater than width 53 to facilitate the placement of buffer core assembly 24 in container 12.

Vertical ridges 48 and 50 extend along the height of container 12 where wall recesses 44 and 46 open to inner side walls 28 and 30 toward front wall 26 of container 12. Vertical ridges 48 and 50 abut buffer core assembly 24 in its installed position, as will be discussed in further detail below.

Buffer core assembly 24 includes gel cassettes 16 and 18, which are placed on front side 54 and back side 56 of buffer core body 14 to form a portion of the sides of upper buffer chamber 52. Upper buffer chamber 52 holds a second electrically chargeable buffer solution. In practice, upper buffer chamber 52 often is referred to as the anode chamber or the cathode chamber, depending on the polarity of the electric charge applied to the buffer solution contained in upper buffer chamber 52.

Buffer core body 14 generally is U-shaped, and includes spaced-apart upraised side members 58 and 60, base 62 and beam 64. Beam 64 provides support for and connects side members 58 and 60, and is positioned approximately half-way between the front and back sides of buffer core body 14. Flanges 66 and 68 are located at the top portions of side members 58 and 60, respectively. Buffer core body 14 also has front inset 70 and rear inset 72.

Gel cassettes 16 and 18 are positioned on each of the front and rear sides of buffer core body 14 in a sandwiched fashion. Gel cassettes 16 and 18 have a front surface 80 and a back surface 82. Each gel cassette includes a pair of thin wall plates that are commonly referred to as the divider or divider plate 84 and the retainer or retainer plate 86. Retainer plate 86 is slightly shorter in height than divider plate 84.

Divider plate 84 is affixed to a peripheral ridge (not shown) along the lateral sides and the bottom periphery of retainer plate 86 to define an internal gel compartment 88 for holding an electrophoresis gel (not shown). Gel compartment 88 has a comb opening 90 at the top portion of the cassette for receiving a sample that is to be electrophoretically separated. Located along the lower portion of divider plate 84 and traversing the width of each of gel cassettes 16 and 18 is an opening 92 that opens gel compartment 88 to the exterior of the cassette.

Gel cassettes suitable for the present application are known in the art. In a typical gel cassette, the gel is pre-filled within the internal gel compartment for ease of handling. The comb opening 90 is closed with a comb (not shown) and opening 92 is masked closed with a removable tape (not shown). An example of the gel cassettes that are suitable for this application are the 12% Tris-glycine gels sold by Novel Experimental Technology, Incorporated of San Diego, Calif., Catalog No. EC6005. Gel cassettes of similar types are also commercially available from other sources.

Gel cassettes 16 and 18 are positioned adjacent each of front side 54 and back side 56 of buffer core body 14 in a sandwiched fashion to define upper buffer chamber 52 for receiving the second buffer solution (not shown). As will be described in more detail below, the second buffer solution is isolated from the first buffer solution in container 12. In view of the isolation of the two buffer solutions, the portion of container 12 that contains the first buffer solution is often referred to as the lower buffer chamber, as distinguished from upper buffer chamber 52.

Both the front and the rear surfaces of buffer core body 14 are provided with grooves 94 and 96 for fitting and holding resilient strips 98 and 100, respectively, as a seal between the gel cassettes and buffer core body 14. The seal ensures isolation of the second buffer solution in upper buffer chamber 52 from the first buffer solution in container 12, and provides a cushion to reduce excess stress along the force bearing surfaces of the cassettes when they are held against buffer core body 14.

Figure 5:
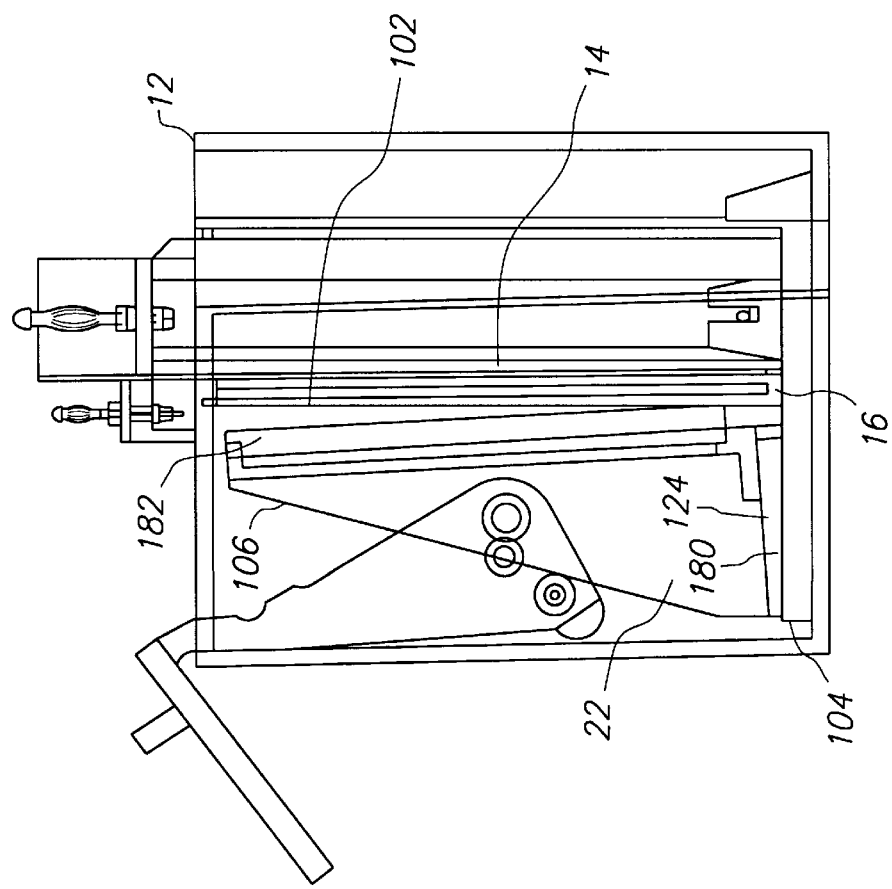
FIG. 5 is a side view of an electrophoresis cell assembly that includes an exemplary embodiment of the cam device of this invention in the unclamped position.

Prior to the use of gel cassettes 16 and 18, the comb (not shown) and the tape (not shown) are removed. The sample to be analyzed is introduced into the gel compartment 88 through the comb opening 90 by appropriate means such as a pipette. Buffer core assembly 24 is then slidably inserted into wall recesses 44 and 46 from the top of container 12 to rest on risers 104 (one of which is shown in FIG. 5) inside container 12. Risers 104 elevate buffer core assembly 24 to permit the first buffer solution to pass below and surround the front and back sides of buffer core assembly 24. Buffer core assembly 24 is then moved toward front wall 26 of container 12 such that side ridges 102 of gel cassette 18 are aligned coincidentally with and bear upon vertical ridges 48 and 50.

Although the above description refers to the use of two gel cassettes as part of buffer core assembly 24, the present invention may also be used with a single cassette. In such cases, a single cassette can be installed on one side of buffer core body 14, and a blank or a plate member can be placed on the other side to achieve similar performance and results with assured consistency and uniformity.

Figure 2:
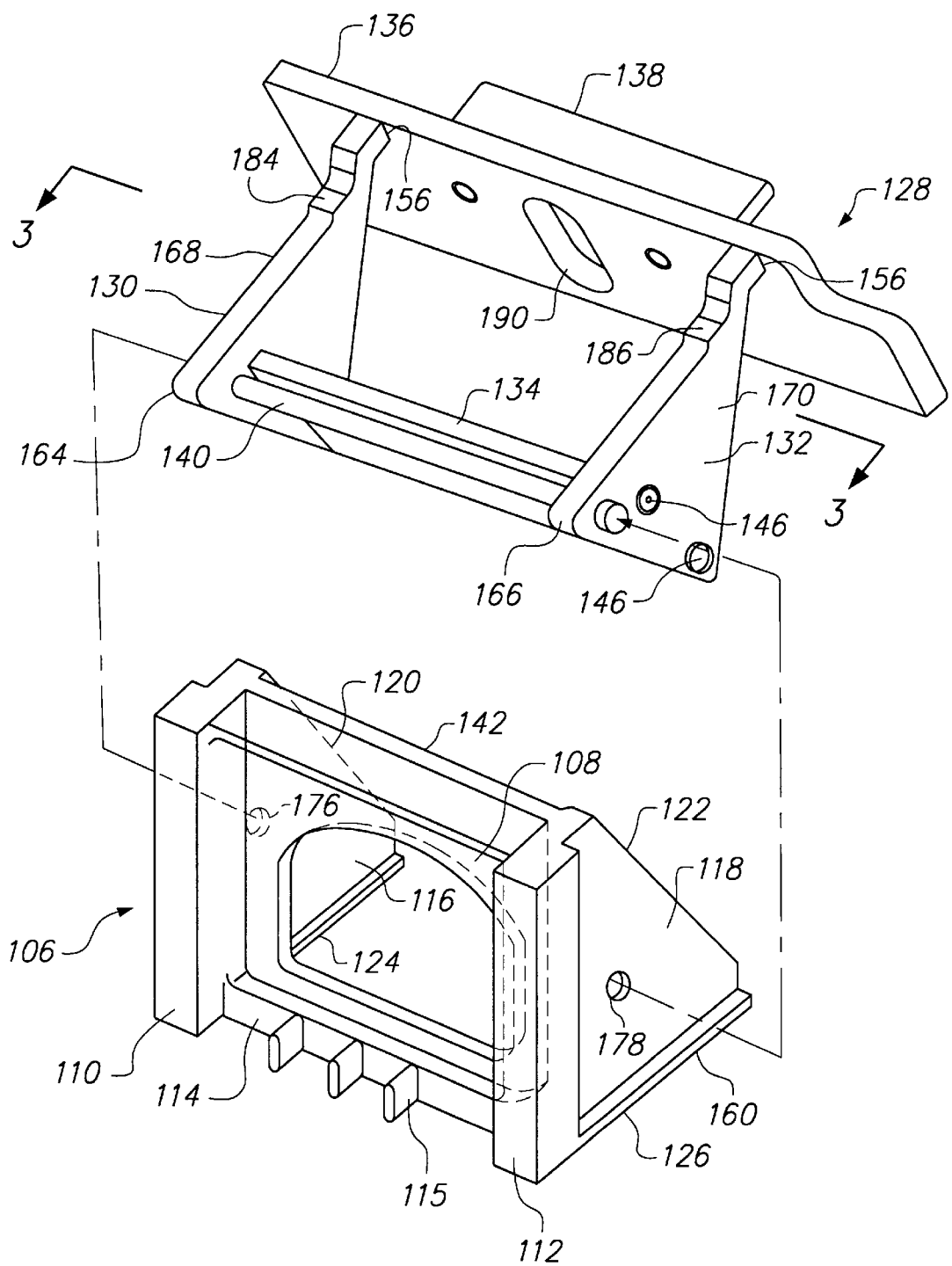
FIG. 2 is an exploded perspective view of an embodiment of the mounting block and cam arm assembly of this invention.

Referring now also to FIG. 2, a first illustrative embodiment of cam device 22 of the present invention used to secure buffer core assembly 24 in container 12 is described. Cam device 22 comprises mounting block 106 and cam arm assembly 128. Mounting block 106 includes a generally square or rectangular front panel 108 and contact surfaces 110 and 112 on the lateral sides of front panel 108. At the lower portion of base 114 of front panel 108, a plurality of upraised push tabs 115 are provided to bear upon bottom edge 99 of divider plate 84 (shown in FIG. 1).

Affixed to the reverse side of front panel 108, a pair of spaced apart parallel side panels 116 and 118 are provided to enhance structural integrity of mounting block 106 and to support it in an erect position. Side panels 116 and 118 substantially align with contact surfaces 110 and 112, respectively. Bases 124 and 126 of side panels 116 and 118 extend from back surface 142 of front panel 108. Inclined edges 120 and 122 extend from the top of contact surfaces 110 and 112 to bases 124 and 126.

Figure 3:
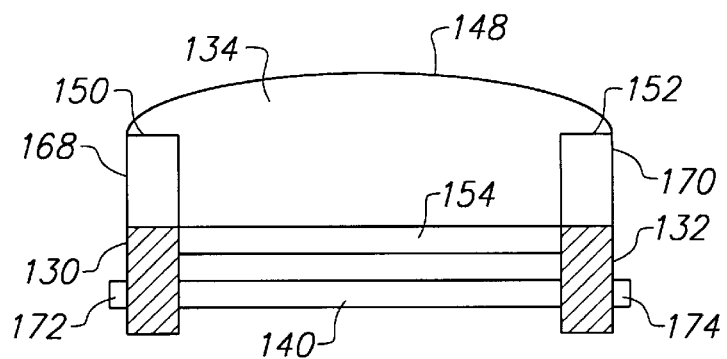
FIG. 3 is a partial sectional view along line 3—3 of FIG. 2.

Cam arm assembly 128 includes cam arms 130 and 132, cam 134, top plate 136, grip 138 and axle 140. Cam arms 130 and 132 are affixed to sides of cam 134 by suitable fasteners, for example, screws 146, or suitable adhesive, such as epoxy. As shown in FIG. 3, cam 134 also is affixed to cam arms 130 and 132 at ends 150 and 152. Cam 134 includes edge 154 and curved end 148 extending between cam arms 130 and 132.

Referring again to FIG. 2, top plate 136 and grip 138 form a handle used to pivot cam arm assembly 128 relative to mounting block 106. Top plate 136 is attached by suitable fasteners to top ends 156 and 158 of cam arms 130 and 132, respectively. Oval-shaped recess 190 provides clearance for tab 188 of container 12 (shown in FIG. 1). Grip 138 is attached to the top surface of top plate 136 or alternatively may be attached to cam arms 130 and 132.

As shown in FIGS. 2 and 3, axle 140 extends through holes (not shown) near curved ends 164 and 166, and terminates at tips 172 and 174 that extend beyond outer surfaces 168 and 170 of cam arms 130 and 132, respectively. Axle 140 is securely attached to cam arms 130 and 132 by suitable means, for example, epoxy. Axle 140 freely pivots in holes 176 and 178.

Mounting block 106 and cam arm assembly 128 can be fabricated from a number of materials by a variety of methods. In the embodiments described herein, and by way of example only, mounting block 106 is formed by injection molding of acrylic plastic, and cam arm assembly 128 may be constructed from delrin, or other suitable inert plastic material such as nylon. Alternatively, cam arm assembly 128 may be formed as a single unit by injection molding.

Figure 4A:
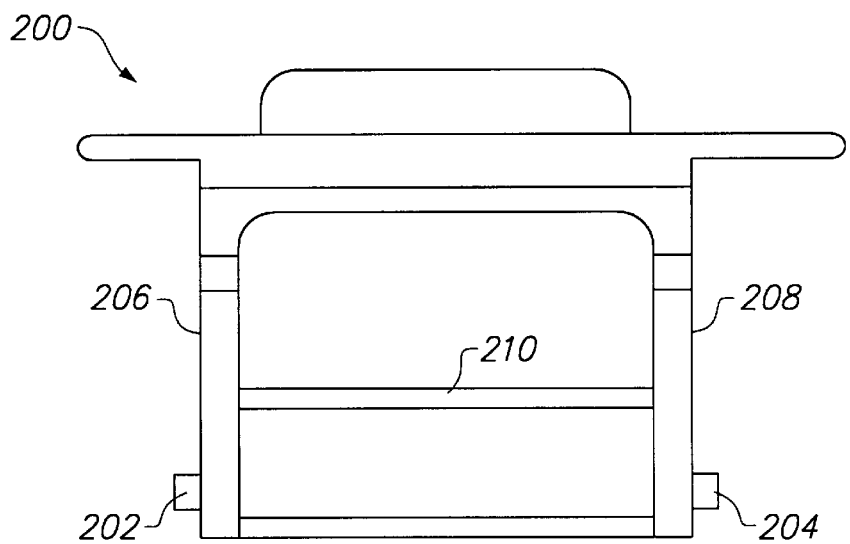
FIG. 4A is a front view of an alternative embodiment of a cam arm assembly of the present invention.
Figure 4B:
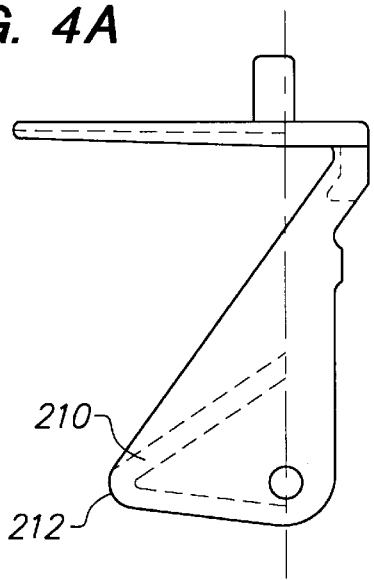
FIG. 4B is a side view of the cam arm assembly of FIG. 4A.

FIGS. 4A and 4B show an alternative embodiment of cam arm assembly 200. Cylindrical side tabs 202 and 204 are integral with and extend from cam arms 206 and 208, respectively, and are disposed to pivot in holes 176 and 178 of mounting block 106. V-shaped cam 210 is formed integrally with cam arms 206 and 208. Cam 210 includes curved end 212 (similar to curved end 148 in FIG. 3) extending between cam arms 206 and 208. Cam arm assembly 200 may be fabricated as a single unit, for example by injection molding.

FIG. 5 illustrates cam device 22 inserted into container 12 with cam arm assembly 128 disposed in an open position toward back wall 32 of container 12. On insertion, mounting block 106 is disposed adjacent gel cassette 16 at back side 56 of buffer core assembly 24. Base 124 of side panel 116 includes tapered bottom edge 180 that rests on riser 104. Although not shown in FIG. 5, base 126 of side panel 118 similarly includes tapered bottom edge 160 (shown in FIG. 2) that rests on a riser disposed near side wall 30 of container 12. As shown in FIG. 5, upon initial insertion into container 12, mounting block 106 is positioned so that top portion 182 of contact surfaces 110 and 112 (not shown) are disposed away from side ridges 102 of gel cassette 16.

Figure 6:
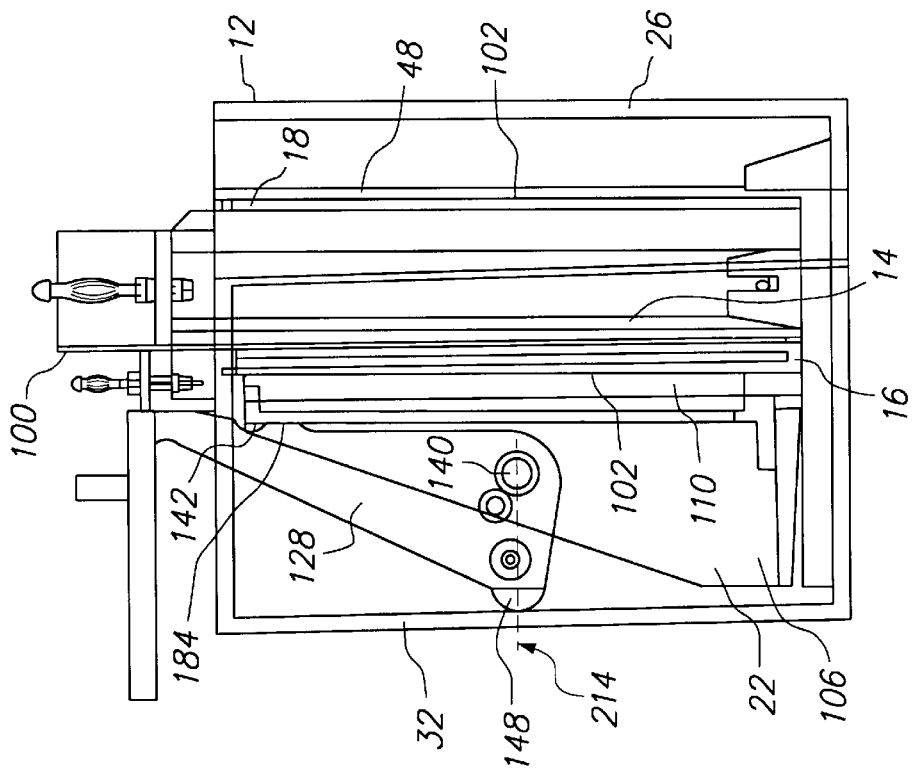
FIG. 6 is a side view of an electrophoresis cell assembly that includes an exemplary embodiment of the cam device of this invention in the clamped position.

FIG. 6 illustrates cam device 22 with cam arm assembly 128 in a closed position. In particular, cam arm assembly 128 is shown rotated forward toward front wall 26 of container 12. As cam arm assembly 128 is rotated forward, curved end 148 bears against back wall 32, causing mounting block 106 to pivot forward on tapered bottom edges 160 and 180 toward gel cassette 16. As a result, contact surfaces 110 and 112 (not shown) align with and bear upon side ridges 102 of gel cassette 16, pressing gel cassette 16 against buffer core body 14. Buffer core body 14 in turn bears upon gel cassette 18, pressing side ridges 102 of gel cassette 18 against vertical ridges 48 and 50 (not shown). As cam arm assembly 128 is further rotated forward, curved end 148 passes through a plane extending perpendicularly from back wall 32 to the center of axle 140 (shown as dashed line 214 in FIG. 6). Cam 134 therefore goes "over center" at a point where curved end 148 exceeds the point of maximum pressure against back wall 32, thus locking cam device 22 in position. Because force would be required to return cam arm assembly 128 backward past plane (i.e., returning curved end 148 below dashed line 214), the over-center cam 134 secures mounting block 106 against gel cassette 16. Upon further forward motion of cam arm assembly 128, flat portions 184 and 186 (not shown) of cam arms 130 and 132, respectively, contact back surface 142 of front panel 108, providing a positive stop that prevents cam arm assembly 128 from further forward movement.

As contact surfaces 110 and 112 (not shown) of mounting block 106 bear on side ridges 102, a bearing force is transmitted through gel cassettes 16 and 18 against resilient strips 100 and 98 (not shown), respectively on buffer core body 14 to seal upper buffer chamber 52. This ensures fluid and electrical isolation between the first and second buffer solutions in container 12 and in upper buffer chamber 52 to prevent mixing of the two buffer solutions, which can interfere with proper molecular separation. It also reduces the risks of electrical grounding of the power supply or other sensitive instruments used in connection with the electrophoresis. The resiliency of the strips 98 and 100 also provides a means of resistance against the bearing force of mounting block 106 such that a static balance is maintained among buffer core body 14, gel cassettes 16 and 18, mounting block 106, cam arm assembly 128 and back wall 32 of container 12, thereby securing them in container 12.

Cam device 22 provides a consistent and reproducible clamping force to buffer core assembly 24. In particular, because cam arm assembly 128 is pivotally coupled to mounting block 106, mounting block 106 cannot slip relative to cam arm assembly 128, and thereby inadvertently release pressure on buffer core assembly 24. Further, once cam 134 goes "over center," cam device 22 is locked in position and applies a consistent and reproducible clamping force to buffer core assembly 24 that does not depend upon the amount of force applied to top plate 136 and grip 138.

In application, buffer core assembly 24 and cam device 22 are first secured within container 12 in the manner as described above. A first buffer solution is dispensed into the upper buffer chamber 52 above the comb openings 90 of gel cassettes 16 and 18 to establish fluid contact with the gel in the gel compartments. A second buffer solution is then introduced into container 12 until its level is approximately that of beam 64. Lid 20 is then positioned above the front portion of container 12, the conductor cables are attached to a power supply system or charging means (not shown) and electrophoresis commences.

It will be apparent from the foregoing that although particular forms of the invention have been illustrated and described, various modifications can be made without departing from the spirit and scope of the invention. For example cam arm assembly 128 may be fabricated as a single unit by injection molding or other similar technique. Accordingly, it is not intended that the invention be limited, except as by the appended claims.

I claim:

1. An apparatus for securing an electrophoresis gel cassette to a buffer core body in an electrophoresis container, the apparatus comprising:
    a mounting block having a first surface adapted to engage the buffer core body, the mounting block configured for insertion between a back wall of the container and the gel cassette; and
    a cam pivotally coupled to the mounting block, the cam slidingly engaging the back wall of the container to urge the first surface to secure the gel cassette to the buffer core body.

2. The apparatus of claim 1, wherein the cam locks the mounting block into engagement with the gel cassette.

3. The apparatus of claim 1, wherein the mounting block further has a second surface adapted to prevent further urging of the first surface toward the buffer core body.

4. The apparatus of claim 1 further comprising an axle pivotally coupling the cam to the mounting block.

5. The apparatus of claim 1 further comprising first and second cylindrical tabs pivotally coupling the cam to the mounting block.

6. The apparatus of claim 1 further comprising a handle coupled to the cam to pivot the cam relative to the mounting block.

7. The apparatus of claim 1, wherein the cam further has a curved end that slidingly engages the back wall of the container.

8. The apparatus of claim 1, wherein the mounting block further has a bottom edge adapted to facilitate urging the first surface against the buffer core body.

9. An apparatus for securing an electrophoresis gel cassette to a buffer core body in an electrophoresis container, the container having a first side wall defining a first recess and a second side wall defining a second recess, the buffer core body disposed in the container and having portions disposed in the first and second recesses, the apparatus comprising:
    a mounting block having a front panel and first and second side panels, the front panel having a first surface adapted to engage the buffer core body, the mounting block configured for insertion between a back wall of the container and the gel cassette; and
    a cam pivotally coupled to the first and second side panels, the cam slidingly engaging the back wall of the container to urge the first surface to secure the gel cassette to the buffer core body and lock the mounting block into engagement with the gel cassette.

10. The apparatus of claim 9, wherein:
    the front panel further has a back surface; and
    the cam has a portion that contacts the back surface to prevent further urging of the first surface toward the buffer core body.

11. The apparatus of claim 9, wherein the apparatus further comprises first and second opposed cam arms, the first cam arm affixed to a first end of the cam, the second cam arm affixed to a second end of the cam, the first and second cam arms pivotally coupled to the first and second side panels.

12. The apparatus of claim 11 further comprising an axle extending between the first and second cam arms, the axle having first and second ends, the first end extending through a hole in the first cam arm to freely pivot in a hole in the first side arm, the second end extending through a hole in the second cam arm to freely pivot in a hole in the second side arm.

13. The apparatus of claim 11 further comprising:
    a first cylindrical tab extending from the first cam arm and adapted to freely pivot in a hole in the first side arm; and
    a second cylindrical tab extending from the second cam arm and adapted to freely pivot in a hole in the second side arm.

14. The apparatus of claim 11 further comprising a handle coupled to the first and second cam arms to pivot the cam relative to the mounting block.

15. The apparatus of claim 9, wherein the cam further has a curved end that slidingly engages the back wall of the container.

16. The apparatus of claim 9, wherein the first side panel has a bottom edge and the second side panel has a bottom edge, the bottom edges adapted to facilitate urging the first surface against the buffer core body.

17. A method for securing an electrophoresis gel cassette to a buffer core body in an electrophoresis container, the method comprising:
    providing a mounting block having a first surface adapted to engage the buffer core body;
    providing a cam pivotally coupled to the mounting block;
    inserting the mounting block between a back wall of the container and the gel cassette; and
    slidingly engaging the cam against a back wall of the container to urge the first surface to secure the gel cassette to the buffer core body.

18. The method of claim 17 wherein the engaging step causes the cam to lock the mounting block into engagement with the gel cassette.

19. The method of claim 17 further comprising providing on the mounting block a second surface adapted to prevent further urging of the first surface toward the buffer core body.

20. The method of claim 17 further comprising providing a handle coupled to the cam to pivot the cam relative to the mounting block.

* * * * *